(12) United States Patent
Dinkelborg et al.

(10) Patent No.: US 6,342,201 B1
(45) Date of Patent: Jan. 29, 2002

(54) COMPLEX COMPOUNDS FOR DIAGNOSIS OF VASCULAR DISEASES

(75) Inventors: Ludger Dinkelborg; Christoph Stephan Hilger, both of Berlin; Wolfhard Semmler, Glienicke; Ulrich Speck; Peter Henklein, both of Berlin, all of (DE)

(73) Assignee: Institut for Diagnostikforschung GmbH an der Freien Universitat, Berlin (DE)

( * ) Notice: Subject to any disclaimer, the term of this patent is extended or adjusted under 35 U.S.C. 154(b) by 0 days.

(21) Appl. No.: 08/765,953

(22) PCT Filed: Jun. 21, 1995

(86) PCT No.: PCT/DE95/00837

§ 371 Date: Jul. 17, 1997

§ 102(e) Date: Jul. 17, 1997

(87) PCT Pub. No.: WO96/02568

PCT Pub. Date: Feb. 1, 1996

(30) Foreign Application Priority Data

Jul. 13, 1994 (DE) .......................... 44 25 778

(51) Int. Cl.$^7$ .................. A61K 51/00; A61M 36/14
(52) U.S. Cl. .................. 424/1.69; 424/1.11; 424/1.65; 424/9.1; 530/300; 534/14
(58) Field of Search .................. 424/1.11, 1.65, 424/1.69, 9.1; 530/300, 324–330, 333–338; 534/7, 10–16

(56) References Cited

FOREIGN PATENT DOCUMENTS

| EP | 606683 | * | 7/1994 |
| WO | 9116919 | * | 11/1991 |
| WO | 9312819 | * | 7/1993 |
| WO | 9422497 | * | 10/1994 |

OTHER PUBLICATIONS

Dinkelborg et al, J. Nuclear Medicine, vol. 36, Suppl. 5, p. 102 P, "Endothelin Derivatives for Imaging of Atherosclerosis.", Jun. 15, 1995.*

Kurata et al, J. Nuclear Medicine, vol. 33, No. 5, p. 845, "Localization of Radioodinated Endothelin–1 in injured aortic tissue of cholesterol fed rabbits", May 1992.*

Doherty, J. Medicinal Chemistry, vol. 35, No. 9, pp. 1493–1508, "Endothelin: A New Challenge", May 1992.*

* cited by examiner

*Primary Examiner*—Dameron Jones
(74) *Attorney, Agent, or Firm*—Millen White Zelano & Branigan (57) ABSTRACT

The present invention concerns novel complexes for use in the diagnosis of vascular diseases, methods of manufacturing such complexes and diagnostic agents containing them. These complexes strongly enrich themselves in atherosclerotic plaques and are thus suitable for use in non-invasive procedures for diagnosing atherosclerosis.

15 Claims, 2 Drawing Sheets

COMPLEX COMPOUNDS FOR DIAGNOSIS OF VASCULAR DISEASES

This application is a 371 of PCT/DE95/00837 filed Jun. 21, 1995.

The invention concerns new complex compounds for the diagnosis of vascular diseases, processes for their production as well as diagnostic agents containing these compounds.

Arteriosclerosis is a chronic, progressive disease of the blood vessels, which previously could only be clinically diagnosed at an advanced stage. Vessel change caused through arteriosclerosis are today conventionally determined through arteriography. Here a contrasting agent is applied via a catheter into the vessel of interest and stenosis of the regions of the vessel is detected through X-rays. A disadvantage of this procedure is that only partial regions of the vascular system can be observed. Because arteriography is an invasive procedure, complications can arise upon its application like for example pain, perforation of an artery, arrhythmia, heart attack or stroke, and under unfortunate circumstances even death of the patient.

Furthermore procedures based on the application of ultrasound as well as MR-tomography are also used for the diagnosis of arteriosclerosis.

All the presently used procedures have the great disadvantage in that the arteriosclerotic vessel change is detected through the observation of contracted blood flow or significant changes in the artery wall and therefore detected only at an advanced stage of atherogenesis.

Early detection of arteriosclerosis would be of great significance for example for the control of therapeutical effect of diet, calcium antagonists, lipid- and high blood pressure reducers, the control of restenosis after angioplasty and the diagnosis of coronary heart diseases as well as the detection of thrombotic vessel deposition.

Non-invasive techniques for the diagnosis of arteriosclerosis have been described. Radioactive labeled antibodies or also labeled low density lipoproteins (LDL) are introduced which bind on the arteriosclerotic wall regions (Lees et al. 1993, J. Nucl. Med. 24, 154–156; Kaliman et al. 1985, Circulation, 72, 300; Virgolini et al. 1991, Eur. J. Nucl. Med., 18, 944–947). These methods however have decisive disadvantages, for example the antigenic effect of the antibodies on the organism and the long duration (several days) necessary for the isolation, purification and labelling of LDL from the patient's blood. These large molecules also reveal a long half life in the blood which together with a high background radiation over the whole body making the localization of arteriosclerotic lesions difficult if not impossible.

Shih et al. (1990, Proc. Natl. Acad. Sci., 87, 1436–1440) have synthesized partial sequences of the LDL-protein portions (apo-B-100), which although still bind to arteriosclerotic plaque, reveal an overall shorter half-life in blood and a better signal-noise ratio. Due to their low affinity to plague and/or the low density of binding sites for this apo-B-peptide in the plaque, a successful in vivo diagnosis of arteriosclerosis could not be established.

The object of the invention is to provide new compounds and agents which are suitable for non-invasive diagnostic procedures, especially for the diagnosis of early, but not yet stenotic, vascular diseases.

Endothelines are physiologically active peptides, which perform hormonal as well as neuroregulatory functions in organisms (MacCumber et al. 1989, Proc. Natl. Acad. Sci., 7285–7289; Yanagisawa et al. 1989, Trends Pharmacol. Sci., 10, 374–378; LeMonier die Gouville et al., 1989, Life Scd., 45, 1499–1513; Yanagisawa et al., 1988, Nature, 332, 411–415). Up to now four different isotypes have been identified in humans (Inoue et al., 1989, Proc. Natl. Acad. Sci., 86, 2863–2867). Endotheline 1 is a polypeptide having the following sequence of 21 amino acids:

Cys-Ser-Cys-Ser-Ser-Leu-Met-Asp-Lys-Glu-Cys-Val-Tyr-Phe-Cys-His-Leu-Asp-Ile-Ile-Trp (Yanagisawa et al., 1988, Nature, 332, 411–415).

From vascular endothelium an inactive precursor of the endotheline, the Big Endotheline, is formed. After a heptadecapeptide is splitted off through the Endotheline-Converting-Enzyme (ECE) endotheline originates, which binds on specific receptors of smooth vascular musculature. There it leads to a $Ca^{++}$-facilitated contraction of the smooth muscle cells (Yanagisawa et al., Nature, 332, 411–415; Takuwa et al. 1991, Contrib. Nephrol., 90, 99–104).

One of the early irreversible changes arising from atherogenesis is, among others, the proliferation of smooth muscle cells of the vessel wall brought about by the growth factor (e-g. PDGF) (Desmoulière and Gabbiani 1992, Cerebrovasc. Dis., 2, 63–71). Through in vitro incubation of human atheromatotic coronary arteries with $^{125}$I-endotheline 1, it could be shown that an increased binding of $^{125}$I-endotheline 1 in the region of Tunica media as well as Vasa vasora region appears (Dashwood et al., 1991, J. Cardiovasc. Pharmacol., 17, 458–462). Through the application of $^{125}$I-endotheline 1 in rabbits, whose abdominal aorta were previously de-endothelisized via a balloon catheter, an increased uptake of $^{125}$I-endotheline 1 in the de-endothelisized regions of the aorta could be shown, which indicates a greater density of binding sites for endotheline 1 in the damaged vessel regions (Kurata et al. 1992, J. Nucl. Med., 33, 845). From this investigation it can be concluded that the proliferated smooth muscle cells also further express endotheline receptors.

Endotheline 1 has a strong vasoconstrictory effect on smooth vascular musculature (A. M. Doherty, 1992, Medical Chemistry, 35, 1493–1508). Therefore, it can only be applied i.v. relative low concentrations into the organism. Higher concentrations can only be applied with partial sequences of endothelines, endotheline derivatives, endotheline analogs or endotheline antagonists, which although bind to the endotheline receptor, but do not lead to such a marked contraction of the smooth muscle cells.

Since endothelines are eliminated very quickly through the kidneys, disturbing background radiation caused by the uptake of endothelines by other organs or tissues is extremely low.

The German patent application P 43 01 871.8 already describes compounds containing endothelines, partial sequences of endothelines, endotheline derivatives, endotheline antagonists or endotheline analogs, which bind to endotheline receptors.

During the search for additional compounds the substance was found which has the general formula I $$(K)_z\text{-}(L)_y\text{-}(A^1)_{aa}\text{-}(A^2)_{bb}\text{-}(A^3)_{cc}\text{-}(A^4)_{dd}\text{-}(A^5)_{ee}\text{-}(A^6)_{ff}\text{-}(A^7)_{gg}\text{-}(A^8)_{hh}\text{-}(A^9)_{jj}\text{-}(A^{10})_{kk}\text{-}(A^{11})_{ll}\text{-Ile-Ile-Trp} \quad (I)$$

in which
  aa, bb, cc, dd, ee, ff, gg, hh, jj, kk and ll stand for, independent from one another, the integers 0, 1 or 2,
  y and z represent independent from one another the integers 0 or 1,
  K depicts a chelate-forming residual having the general formula IIA or IIB (IIA)

(IIB)

in which
T is a hydrogen atom or a bond at a metal atom or a suitable sulfur protecting group like an alkali metal ion, a $C_{1-6}$-acyl residual, a benzoyl residual, a hydroxyacetyl residual, an acetamidomethyl residual, a p-methoxybenzyl residual, an ethoxyethyl residual, a benzyl residual, an ortho- or para-hydroxybenzyl residual, an ortho- or para-acetoxybenzyl residual, a p-nitrobenzyl residual, a 4-picolyl residual, a 2-picolyl-N-oxid residual, a 9-anthrylmethyl residual, a 9-fluorenyl residual, a ferrocenylmethyl residual, a diphenylmethyl residual, a bis(4-methoxyphenyl)methyl residual, a dibenzosuberyl residual, a triphenylmethyl residual, a diphenyl-4-pyridylmethyl residual, a phenyl residual, a 2,4-dinitrophenyl residual, a tert-butyl residual, a 1-adamantyl residual, a methoxymethyl residual, a isobutoxymethyl residual, a 2-tetrahydropyranyl residual, a benzylthiomethyl residual, a phenylthiomethyl residual, a trimethylacetamidomethyl residual, a benzamidomethyl residual, an acetylmethyl residual, a carboxymethyl residual, a cyanomethyl residual, a 2-nitro-1-phenylethyl residual, a 2-(4'-pyrdyl)ethyl residual, 2-cyanoethyl residual, a 2,2-bis(carboethoxy)ethyl residual, a 1-m-nitrophenyl-2-benzoylethyl residual, a 2-phenylsulfonylethyl residual, a 1-(4-methylphenylsulfonyl)-2-methylprop-2-yl residual, a silyl residual, a N-{[(p-biphenyl)isopropoxy]carbonyl}-N-methyl-γ-aminobutyrate residual, a N-(tert.-butoxycarbonyl)-N-methyl-γ-aminobutyrate residual, a 2,2,2-trichlorethoxycarbonyl residual, a tert.-butoxycarbonyl residual, a benzyloxycarbonyl residual, a p-methoxybenzyloxycarbonyl residual, a N-ethyl residual, a N-methoxymethyl residual, a S-ethyl residual, a tert.-S-butyl residual, a substituted S-phenyl residual, a sulfonate residual, a sulfenylthiocarbonate residual or a 3-nitro-2-pyridinsulfenyl residual, or whereby two T residuals form together with those attached S atoms inter- or intramolecular disulfide bridges, $R_4$ stands for a residual having the formula IIC or IID (IIC)
—CH₂—CH—
            |
            C=O
            |

(IID)
—CH—(CH₂)₂—
  |
  C=O
  | where
the *-marked carbon atoms are bound to the imino group of the formula IIB and
n' stands for the integers 1 or 2,
i for any number from 2 to 6, and TT for residuals of α-amino acids like alanine, valine, leucine, isoleucine, proline, tryptophane, phenylalanine, methionine, glycine, serine, tyrosine, threonine, cysteine, asparagine, glutamine, aspartic acid, glutamic acid, lysine, arginine, histidine, citrulline, homocysteine, homoserine, 4-hydroxyproline, 5-hydroxylysine, ornithine, sarcosine or taurine and/ or their homologous β-amino acids, which are bonded in the usual way over the amide groups, as well as chelate forming residuals having the formula IIE

(IIE)

in which
$R_6$ represents a hydrogen or a $C_{1-6}$-alkyl residual, as well as chelate forming residuals having the formula IIF

(IIF)

in which
the residuals $R_7$ to $R_{18}$ each represent independent from one another a hydrogen atom, a $C_{1-10}$-alkyl chain and/or a bond on L, and o, p and r mean each the numbers 1 or 2 and T has the above given meaning, as well as chelate forming residuals having the formula IIG

(IIG)

in which
$R_{19}$ to $R_{24}$ are equal or different and depict independent from one another a hydrogen atom or a $C_{1-4}$-alkyl residual,
m' stands for the integers 2 or 3, as well as chelate forming residuals having the formula IIH

(IIH)

in which
X$_1$ means a bond, a methylene group or a CHY$_4$-group, and one of the groups Y$_1$, Y$_2$, Y$_3$ or Y$_4$ stands for a bond to L and the remaining indicate hydrogen or optionally depict an oxygen atom,
T has the above given meaning, and
A$_1$, A$_2$, A$_3$ and A$_4$ are equal or different and represent independent from one another hydrogen or a C$_{1-6}$-alkyl residual, as well as chelate forming residuals having the formula IIJ (IIJ)

in which
R$_{27}$ depicts a hydrogen atom or optionally a C$_{1-6}$-alkyl residual substituted with one or two hydroxyl groups,
R$_{25}$ and R$_{26}$ represent each a hydrogen atom or together an oxygen atom,
A a hydroxyl- or mercapto group,
Y a hydrogen atom, a carboxy- or sulfonyl residual and
Z a carbon atom or a nitrogen atom, as well as chelate forming residuals having the formula IIK, $(AA^1)_{mm}$-$(AA^2)_{nn}$-$(AA^3)_{oo}$-$(AA^4)_{pp}$-$(AA^5)_{qq}$-$(AA^6)_{rr}$ (IIK)

in which
mm, nn, oo, pp, qq and rr stand for, independent from one another, the integers 0, 1 or 2,
AA$^1$ to AA$^6$ stand for, independent from one another, residuals of α-amino acids like alanine, valine, leucine, isoleucine, proline, tryptophane, phenylalanine, methionine, glycine, serine, tyrosine, threonine or cysteine, which optionally bears a T group with the above given meaning instead of the hydrogen atom on the sulfur, asparagine, glutamine, asparatic acid, glutamic acid, lysine, arginine, histidine, citrulline, homocysteine, homoserine, 4-hydroxyproline, 5-hydroxylysine, ornithine, sarcosine or taurine and/or their homologous β-amino acids, which are bonded in the usual way over the amide groups, and whereby optionally each two available cysteine residuals are linked to one another to form one cystine residual, as well as chelating substances having the formula II L, (IIL)

in which
R$^a$, R$^b$, R$^c$, R$^d$, R$^f$, R$^g$ and R$^h$ are equal or different and each stands for a hydrogen atom and/or a branched or non-branched C$_1$–C$_6$-alkyl residual,
R$^e$ depicts a carboxy group or a non-branched, branched, cyclic or polycyclic C$_1$–C$_{60}$-alkyl-, alkenyl-, polyalkenyl-, alkinyl-, polyalkinyl-, aryl-, alkylaryl- or arylalkyl residual, which is optionally substituted with hydroxy-, oxy-, oxo-, carboxy-, aminocarbonyl-, alkoxycarbonyl-, amino-, aldehyd- or alkoxy groups having up to 20 carbons atoms and/or optionally through one or more heteroatoms from the series O, N, S, P, As, Se intermitted and/or substituted,
T has the above given meaning,
L stands for a bond or a hydrogen atom or a non-branched, branched, cyclic or polycyclic C$_1$–C$_{60}$-alkyl-, alkenyl-, polyalkenyl-, alkinyl-, polyalkenyl, aryl-, alkylaryl- or arylalkyl residual, which is optionally substituted with one or more hydroxy-, mercapto-, alkylmercapto-, oxo-, oxy-, carboxy-, aminocarbonyl-, alkoxycarbonyl-, amino-, aldehyd- or alkoxy groups having up to 20 carbon atoms and/or optionally through one or more heteroatoms from the series O, N, S, P, As, Se intermitted and/or substituted,
or depicts a Z$_1$—R—Z$_2$ residual,
in which
R stands for a straight chain, branched, saturated or unsaturated C$_{1-20}$ alkyl residual which is optionally intermitted through one or more oxygen and/or sulfur atoms and/or carbonyl-, —NHCO—, —N(C$_{1-6}$-alkyl)CO—, —NH— and —N(C$_{1-6}$-alkyl) residuals and optionally substituted with hydroxy- and/or epoxy groups,
Z$_1$ and Z$_2$ independent from one another, each is an —O—, —S—, —(C=O)O—, —NH(C=S)NH—, —(C=O)— or —NH(C=S)— group,
or stands for a residual having the formula α

(α)

in which
s and t stand for independent from one another the integers 0, 1, 2 or 3, the ring B indicates a phenyl- or cyclohexyl residual and Z$_1$ and Z$_2$ have the above given meaning,
A$^1$ to A$^{11}$ represent independent from one another L-α- or D-α-amino acid residuals, —NH—CH(Z)—CO— residuals, in which
Z has the meaning
H—, $CH_3$—, $(CH_3)_2CH$—, $(CH_3)_2CH$—$CH_2$—,
$CH_3$—$CH_2$—$CH(CH_3)$—, $CH_3$—S—$(CH_2)_2$—,
HOOC—$CH_2$—,
HOOC—$(CH_2)_2$—, $H_2N$—$(CH_2)_3$—, $H_2N$—C(=NH)—$(CH_2)_3$—,
HO—$CH_2$—, $CH_3$—CH(OH)—, HS—$CH_2$—, HS—$(CH_2)_2$—,
$H_2N$—CO—$CH_2$—, $H_2N$—CO—$(CH_2)_2$—, $(HOOC)_2$CH—$CH_2$—, in which n means the integers 0, 1 or 2,
or residuals or taurine residuals,
as well as their complexes with metal ions having atomic numbers 21–32, 37–39, 42–51 and 57–83 and their water soluble salts,
which surprisingly enrich the arteriosclerotic plaque to an even stronger extent, and because of low background radiation in other tissues and organs resulting from the quick elimination of these substances, they are preferentially suited for non-invasive diagnosis of arteriosclerosis.

Particularly preferred compounds of the general formula I according to the invention are Asp-Gly-Gly-Cys-Gly-Cys-His-Leu-Asp-Ile-Ile-Trp, Asp-Gly-Gly-Cys-Gly-cys-D-Trp-Leu-Asp-Ile-Ile-Trp, Asp-Gly-Gly-Cys-Gly-Cys-Phe-(D-Trp)-Leu-Asp-Ile-Ile-Trp, N-(4-hydroxycarboxy-1-oxo-3-thia-but-1-yl)-Cys-Phe-(D-Trp)-Leu-Asp-Ile-Ile-Trp, N-(4-hydroxycarboxy-1-oxo-3-thia-but-1-yl)-Cys-(D-Trp)-Leu-Asp-Ile-Ile-Trp, N-(4-hydroxycarboxy-1-oxo-3-thia-yl)-Cys-His-Leu-Asp-Ile-Ile-Trp, N-(mercaptoacetyl)-Gly-Gly-Asp-Phe-(D-Trp)-Leu-Asp-Ile-Ile-Trp and N-(mercaptoacetyl)-Gly-Gly-Asp-(D-Trp)-Leu-Asp-Ile-Ile-Trp.

Particularly preferred complex compounds according to the invention are Tc-99m-complex of Asp-Gly-Gly-Cys-Gly-Cys-His-Leu-Asp-Ile-Ile-Trp, Tc-99m-complex of Asp-Gly-Gly-Cys-Gly-Cys-D-Trp-Leu-Asp-Ile-Ile-Trp, Tc-99m-complex of Asp-Gly-Gly-Cys-Gly-Cys-Phe-(D-Trp)-Leu-Asp-Ile-Ile-Trp, Tc-99m-complex of N-(4-hydroxycarboxy-1-oxo-3-thia-but-1-yl)-Cys-Phe-(D-Trp)-Leu-Asp-Ile-Ile-Trp, Tc-99m-complex of N-(4-hydroxycarboxy-1-oxo-3-thia-but-1-yl)-Cys-(D-Trp)-Leu-Asp-Ile-Ile-Trp, Tc-99m-complex of N-(4-hydroxycarboxy-1-oxo-3-thia-but-1-yl)-Cys-His-Leu-Asp-Ile-Ile-Trp, Tc-99m-complex of N-(mercaptoacetyl)-Gly-Gly-Asp-Phe-(D-Trp)-Leu-Asp-Ile-Ile-Trp and Tc-99m-complex of N-(mercaptoacetyl)-Gly-Gly-Asp-(D-Trp)-Leu-Asp-Ile-Ile-Trp.

It was found that the radioactive labelled metal complexes of the general formula I according to the invention concentrated surprisingly strongly at arteriosclerotic vascular lesions and thus reach a sufficient concentration for display with a scintillation camera or other suitable apparatus common in nuclear medicine. Surprising was the finding that the applied substances according to the invention reach this concentration in vivo so fast and the bonding is so stable that even after removal and elimination of the excess substance binding to the receptors, a high and sufficient concentration for diagnosis remains. Furthermore it was surprising that the enrichment takes place preferable at altered, through the most various of ways, artery wall regions which are to be diagnosed, even though endotheline itself is effective on all vascular areas.

The applied substances according to the invention possess the additional advantage that in contrast to many other substance classes and substances tested, they do not concentrate additionally and nonspecifically in other tissues and organs which is decisive for suitablility as a diagnostic.

Scintigrams show the enrichment in vivo of the compounds according to the invention.

BRIEF DESCRIPTION OF THE DRAWINGS

A left lateral scintigram of a WHHL-rabbit (A) and a New Zealand control rabbit (B) 0.5 h after i.v. application of 74 MBq Tc-99m-complex of Asp-Gly-Gly-Cys-Gly-Cys-Phe-(D-Trp)-Leu-Asp-Ile-Ile-Trp (cf. Example 3 c) show that enrichment activity is visible in vivo in the region of the aortic arch, the left a. carotis as well as in the region of the abdominal aorta of the WHHL-rabbit (A) in contrast to the control rabbit(B). An anterior scintigram of a New Zealand rabbit whose right a. carotis was four weeks earlier denuded with the help of a Fogarty-catheter (A), 0.5 h after i.v. application of 74 MBq Tc-99m-complex of Asp-Gly-Gly-Cys-Gly-Cys-(D-Trp)-Leu-Asp-Ile-Ile-Trp (cf. Example 2 c), as well as an autoradiogram (B1) and Sudan-III-dyeing (B2) of the dissected thoracic aorta of the denuded and the untreated a. carotis 5 h after i.v. application. The order of the dissected tissues for each B1 and B2 from left to right: thoracic aorta, right denuded a. carotis and left untreated a. carotis. The strongly arteriosclerotic right a. carotis could be detected in vivo (A). The in vitro investigations (B1 and B2) confirmed the good correaltion between the higher and more selective accumulation of the compounds according to the invention in the denuded right a. carotis in comparsion to the untreated left a. carotis.

The compounds of the general formula I according to the invention and solutions thereof fulfilled the cited requirements to a surprisingly high degree. They possess both a higher enrichment of pathological tissue regions and a better contrasting property due to favorable pharmacokinetics than previously described diagnostics for the measure of vascular disease. The practical use of the new substances according to the invention is facilitated by their high chemical stability.

In Table 1 the enrichment (cpm/mm$^2$) of the compounds according to the invention in plaque as well as non-plaque regions of the aorta together with the enrichment factor (ratio of enrichment in plaque and enrichment in non-plaque aorta tissue) are displayed. 74 MBq (2 mCi) of the respective compound according to the invention was applied via an ear vein in a WHHL-rabbit. 5 h p.i. the rabbit was killed and both a quantitative autoradiography and a Sudan-III-dyeing of the removed aorta were performed. The so-determined accumulation of the respective compounds according to the invention in the different tissues is listed in Table 1.

TABLE 1

| Example number | Enrichment (cpm/mm$^2$) | | Enrichment factor Plaque / Non-plaque |
| --- | --- | --- | --- |
| | Plaque | Non-plaque | |
| 1 c | 501 | 89 | 6 |
| 2 c | 3090 | 431 | 7 |
| 3 c | 3930 | 368 | 11 |
| 4 c | 3912 | 274 | 14 |
| 5 c | 833 | 98 | 9 |
| 6 c | 353 | 76 | 5 |
| 7 c | 619 | 48 | 13 |
| 8 c | 513 | 52 | 10 |

The complex forming residuals K, which are also present in the complexes according to the invention, must be able to bind to the respective metal ion in the form of coordination and/or covalent bonds.

The complex forming residual K must be selected according to the metal ion to-be-complexed and its charge, oxidation number and atomic and ionic radii, so that an effective and sufficient bond is generated for the implementation according to the invention of the complex according to the invention.

Preferred complex forming residuals are 4-carboxyethylphenylglyoxal-bis-(N-methylthiosemicarbazon)N-hydroxysuccinimidester, 6-(4'-isothiocyanatobenzyl)-3,3,9,9-tetramethyl-4,8-diazaundecan-2,10-dion-dioxime, 2-methyl-2-(4-isothiocyanatobenzyl)-N,N'-propylen-bis-salicylidenamine, 2-methyl-2-(4-isothiocyanatobenzyl)-N,N'-propylen-bis-[5-(sulfo)salicylidenamine, N,N'-bis(2-mercaptopyridyl)methyl]-2-methyl-2-(4-isothiocyanatobenzyl)-1,3-propandiamine, S-benzoylthioacetylglycylglycylglycine, N,N'-bis(benzoylthioacetyl)-2,3-diaminopropionic acid, N,N'-bis(benzoylthioacetyl)-3,4-diaminobutanoic acid, N,N'-bis(benzoylthioacetyl)-4,5-diaminopentane acid, N,N'-1,2-ethylen-di-yl-bis-(2-mercapto-1-carboxyethylamine), Cys(Acm)GlyCys(Acm)GlyGlyArgGlyAspSer.

The preparation of the complexes according to the invention of the compounds of the general formula (I) with the metal ion is achieved using processes well-known to those skilled in the art, in which through a well-known method a radioactive metal ion in the form of its permetallate is reacted with a compound having the general formula (I) in the presence of a reducing agent and optionally an auxiliary ligand.

Preferred metal ions are $^{99m}$Tc or Re in the form of pertechnetate or perrhenate.

The reaction is carried out preferable in an aqueous medium at room temperature. The elimination of the SH-protecting group is achieved in situ or according to literature methods well-known to those skilled in the art, for example through basic hydrolysis, reductive cleavage, etc.

(see for example "Protective Groups in Organic Synthesis", T. W. Greene, John Wiley and Sons 1981).

The preparation of the complexes according to the invention of compounds with the general formula (I) with metal ions can also be achieved in that one reacts in a well-known way a suitable salt or oxide of a suitable radioactive cation with a compund having the general formula (I)

(K)$_z$(L)$_y$-(A$^1$)$_{aa}$-(A$^2$)$_{bb}$-(A$^3$)$_{cc}$-(A$^4$)$_{dd}$-(A$^5$)$_{ee}$-(A$^6$)$_{ff}$-(A$^7$)$_{gg}$-(A$^8$)$_{hh}$-(A$^9$)$_{ii}$-(A$^{10}$)$_{kk}$-(A$^{11}$)$_{ll}$-Ile-Ile-Trp    (I).

Preferred radioactive metal ion are for instance isotopes of Tc and Re.

The preparation of the chelating agents K of the general formula IIA is achieved through procedures well-known in literature (cf. EP 0 248 506) the chloro-acetylation of N-terminal amino groups of di-, tri-, tetra-, penta- or hexapeptides and subsequent conversion of the obtained N-chloroacetylpeptide with alkali metal salts of thiocarbonic acids. An additional procedure for the preparation of the chelating agent K having the general formula IIA follows a well-known method in literature (cf. EP 0 248 506) the reaction of the corresponding activated (for example NHS-ester) and S-acylated thioacetic acid derivatives or 3-thiopropionic acid derivatives with peptides. The activation of the corresponding carbonic acid is achieved according to procedures well-known to those skilled in the art, like for example according to the carbo-diimide method (Fieser, Reagents for Organic Synthesis 10, 142), via a mixed or cyclic anhydride (Org. Prep. Proc. Int. 1975, 7, 215) or via an activated ester (Adv. Org. Chem. Part B, 472).

The production of chelating agent K having the general forumula IIB is achieved through methods well-known in literature (cf. EP 0 248 506) through chloro-actylation of the free amino groups of 1,2-diaminopropionic acid or 1,3-diaminobutanoic acid and subsequent conversion of the obtained N,N'-Dichloroacetyl-diaminocarbonic acid with alkali metal salts of thiocarbonic acid. An additonal process for the preparation of the chelating agent K with the general formula IIB follows a well-known method in literature (cf. EP 0 248 506) the reaction of the corresponding activated (for example NHS-ester) and S-acylated thioacetic acid derivatives or 3-thiopropionic acid derivatives with 1,2-diaminopropionic acid or 1,3-diaminobutanoic acid. The activation of the corresponding carbonic acid is achieved according to procedures well-known to those skilled in the art, like for example according to the carbo-diimide method (Fieser, Reagents for Organic Synthesis 10, 142), via a mixed or cyclic anhydride (Org. Prep. Proc. Int. 1975, 7, 215) or via an activated ester (Adv. Org. Chem. Part B, 472).

The production of the chelating agent K having the general formula IIE is achieved through methods well-known in literature via the conversion of substituted 1,2-dicarbonyl compounds with thiosemicarbazide, as described in the European patent application EP 0 306 168.

The production of the chelating agent K having the general formula IIF is essentially achieved through the reductive amination of sustituted or unsubstituted 1,2-diketo- or 1,3-diketo compounds with substituted, unsubstituted, protected or non-protected aminothiophenes, as described in EP 279 417.

The production of the chelating agent K having the general formula IIG is essentially achieved through methods well-known in literature via the conversion of 2-substituted 1,3-propandiamines with 2-chloro-2-alkyl-3-nitroalkanes, as described in the European patent applications EP 0 417 870 and EP 0 502 594, or through the conversion of 2-substituted 1,3-propandiamines with 1,3-dicarbonylmonoximes to the corresponding imines, which are reduced to the corresponding amines according to well-known methods.

The production of the chelating agent K having the general formula IIH is achieved through methods well-known in literature (cf. U.S. Pat. No. 4,897,255) via chloroacetylation of the free amino group of 1,2- or 1,3-diaminoalkanic acid (see EP 0248506) and subsequently conversion of the obtained N,N'-dichloroacetyldiaminocarbonic acid with alkali metal salts of thiocarbonic acid. An additional process for the production of the chelating agent K having the general formula IIH is achieved through a method well-known in literature (cf. U.S. Pat. No. 4,897,255) through the reaction of the corresponding activated (for example NHS-Ester) and S-protected thiocarbonic acid derivatives with 1,2 or 1,3-diaminoalkanic acid. The activation of the corresponding carbonic acid is achieved according to procedures well-known to those skilled in the art, like for example according to the carbo-diimide method (Fieser, Reagents for Organic Synthesis 10, 142), via a mixed or cyclic anhydride (Org. Prep. Proc. Int. 1975, 7, 215) or via an activated ester (Adv. Org. Chem. Part B, 472).

The production of the chelating agent K having the general formula IIJ is essentially achieved through methods well-known in literature via the conversion of 2-substituted 1,3-propandiamines with optionally an additional carboxyl- or sulfonic acid residual and o-substituted benzaldehydes, subsequent reduction of the obtained Schiff's bases to the corresponding amines and optionally elimination of the protecting groups or through the conversion of substituted malonic acid halides with optionally an additional carboxyl- or sulfonic acid residual and o-substituted benzylamines, as described in the European patent applications EP 0 417 870, EP 0 502 594 and EP 0 502 595.

The production of the chelating agent K with the general formula IIK is achieved via solid phase peptide synthesis (Merrifield, J.Am Chem.Soc., 85 (1963), 2149). The compounds are chemically synthesized according to peptide synthesis methods well-known in literature (e.g. The Practice of Peptide Synthesis, M. Bodanszky and A. Bodanszky; Springer Verlag (1984) and Fieser, Reagenst for Organic Synthesis 10, 142). Here N-protected α-, β- or γ-amino acids are coupled with an activated carbonic acid compound (e.g. acidic chloride, mixed anhydride, activated ester) on N-protected, resin bound amino acids according to processes well-known to those skilled in the art, for example over an addition/elimination reaction of a primary or secondary amine. After the elimination of the amino protecting group according to methods well-known in literature (Solid Phase Peptide Synthesis, A Practical Approach; E. Atherton and R. C. Sheppard; Oxford University Press; Oxford, New York, Tokyo) the remaining amino function is newly derivatized with a N-protected α- β- or γ-Amino acids in a second reaction according to methods well-known in literature. The elimination of the amino protecting group is achieved once again using well-known methods. As N-protected amino acids FMOC-protected derivatives are preferably used. After the construction of the peptide on the resin the finished peptide is cleaved from the resin and for example via preparative HPLC purified (Solid Phase Peptide Synthesis, cf. above).

The preparation of cysteine rich amino acid sequences of metal thionines are achieved in a similar fashion (see patent application WO 91/17173).

The preparation of the chelating forming residuals K of the general formula IIL is achieved according to well-known means.

A preferred preparative variant is characterized in that one reacts cyclic anhydrides of the general formula XX (XX)

in which
$R^a$, $R^b$, $R^c$ and $R^d$ have the above given meaning,
with compounds of the general formula in which the N-terminal amino acid stands for a residual of the general formula The subject matter of the present invention is further a process for the production of the compounds with the general formula I according to the invention as well as their complexes with metal ions of the atomic number 21–32, 37–39, 42–51 and 57–83, which is characterized in that a compound having the general formula II (II)

in which
$A^1$ to $A^{11}$, aa, bb, cc, dd, ee, ff, gg, hh, jj, kk and ll have the meaning defined above
optionally is reacted according to well-known methods with a compound having the general formula III

III whereby
K, L, z and y have the above given meaning, and optionally each reacted according to well-known methods with a radioactive metal ion in its permetallate form in the presence of a reducing agent and optionally auxiliary ligands, or with a salt or oxide of a radioactive cation.

The present invention provides furthermore diagnostic agents, which are characterized by their content of a complex of the compound of the general formula (I) with metal ions of the atomic number 21–32, 37–39, 42–51 and 57–83. Through the appropriate selection of the metal ion the agent is suitable for various diagnostic procedures.

In the case that the agent according to the invention is designated for application in radiodiagnostics, the central ion of the complex salt must be radioactive.

These are especially the ions of the elements with the atomic numbers 27, 29, 30–32, 37–39, 42–51, 62,64,70,75 and 77. Preferred are the isotopes $^{99m}$Tc, $^{186}$Re and $^{111}$In.

Subject matter of the present invention includes further processes for the production of the diagnostic agent according to the invention.

The production of the radiopharmaceutic agent according to the invention is achieved according to well-known means, whereby complexing agents according to the invention with the general formula I and their conjugates—optionally under the addition of additives common in pharmaceutical technology—are dissolved or suspended in aqueous medium and subsequently the solution or suspension is optionally lyophilised or sterilised. Suitable additives are for example physiological safe buffers (like for example tromethamine), additives of auxiliary ligands (like for example sodium citrate or sodium tartrate), reducing agents (like for example tin(II)-chloride) or—if necessary—electrolytes like for example sodium chloride or, if necessary, (one) common pharmaceutical auxiliary agent(s) (for example lactose, methylcellulose, mannite) and/or surfactant(s) (for example lecithine, Tween®, Myrj®). The additives used must allow, with respect to their composition, the production of the compounds according to the invention.

During in vivo nuclear medicine application the agent according to the invention is dosed in amounts of $1 \times 10^{-5}$ to $5 \times 10^4$ nmol/kg body weight, preferentially in amounts between $1 \times 10^{-3}$ to $5 \times 10^2$ nmol/kg body weight. Considering an average body weight of 70 kg the amount of radioactivity for diagnostic application is between 0.05 and 50 mCi, preferentially 5 to 30 mCi per application.

The application is normally carried out via intravenous, intraarterial or peritoneal injection of 0.1 bis 5 ml of a solution of the agent according to the invention. Perferred is intravenous application. Details of such applications and dosages are described for example in "Radiotracers for Medical Applications", CRC-Press, Boca Raton, Fla. The compounds according to the invention are applicable for radiodiagnostics and radiotherapy in the form of their complexes with the radioisotopes of the elements with the atomic numbers 27, 29, 30–32, 37–39, 42–51, 62, 64, 70, 75 and 77.

The radiopharmaceutical agents according to the invention fulfill the various requirements for suitability as radiopharmaceuticals for radiodiagnostics and radiotherapy. Thus they are outstandingly suited, after i.v. application, for the enrichment of targeted tissue and make possible the non-invasive diagnosis of the corresponding tissue. The water solubility of the radiopharmaceutical agents according to the invention is—if necessary—through auxiliary common in pharmaceutical technology as described above guaranteed.

Furthermore the radiopharmaceutical agents according to the invention reveal not only a high stability in vitro but also a high stability in vivo, so that a release or an exchange of the radionucleide bound to the complex does not occur or only to a clinically non-relevant extent.

The production of the pharmaceutical agent according to the invention is also achieved via a well-known method, in which the complexing agent according to the invention is dissolved under the addition of a reducing agent, preferentially tin(II) salts like chloride or tartrate and optionally under the addition of additives common in pharmaceutical technology—in aqueous medium and subsequently sterile filtrated. Suitable additives are for example physiological safe buffers (e.g. tromethamine), minor amounts of electrolyte additives (e.g. sodium chloride), stabilizers (e.g. gluconate, phosphate or phosphonate). The pharmaceutical agent according to the invention exists in the form of a solution or in a lyophilised form and added shortly before the application for example to a solution of Tc-99m-pertechnetate, eluated out of a commercially available generator, or a perrhenate solution.

The production of radiopharmaceuticals is provided according to the invention with a Cold Kit. This Cold Kit contains a compound according to the invention of the general formula (I), a reducing agent and optionally one or more auxiliary ligands in solution, in dry form or in lyophilised form. The Cold Kit includes further an instruction with a reaction regulation for the conversion the compound according to the invention of the general formula (I) with a permetallate of a radioactive metal ion forming a complex according to the invention of the compound of the general formula (I) with the metal ion.

The implementation of the Cold Kit, which consists of a receptacle capable of being closed, which shows a pre-determined amount of endothelines, endotheline derivates, endotheline partial sequences, endotheline analogs and endotheline antagonists are bound on a peptide, a derivative or a chelating agent, which are able to bond metal ions, and moreover contains a sufficient amount of a reducing agent to label the compound with $^{99m}$Tc and serve for the production of a radiopharmaceutical preparation, is also an object of the present invention.

Subject of the present invention is further a process for the graphic presentation of pathological vascular changes, which are distinguished in that a complex of the general formula (I) with a metal ion having an atomic number 21–32, 37–39, 42–51 and 57–83 is applied as the contrasting agent.

In one method for the implementation of a radiodiagnostical investigaton, the radiopharmaceutical composition is delivered in an amount of 0.1 to 30 mCi, preferably from 0.5 to 10 mCi per 70 kg body weight of the patient and the radiation given off by the patient is recorded.

The following examples illustrate the invention:

EXAMPLE 1 a) Synthesis of Asp-Gly-Gly-Cys-Gly-Cys-His-Leu-Asp-Ile-Ile-Trp.

Asp-Gly-Gly-Cys-Gly-Cys-His-Leu-Asp-Ile-Ile-Trp is prepared according to Barany and Marrifield, The Peptides: Analysis, Biology, Academic Press, New York, 1980; Stewart and Young, Solid-Phase Peptide Synthesis, 2nd ed., Pierce Chemical Co., Rockford, Ill., 1984.

Molecular weight:

calc. 1288.4 obs. 1288 (FAB-MS)

b) $^{99m}$Tc-Complex of Asp-Gly-Gly-Cys-Gly-Cys-His-Leu-Asp-Ile-Ile-Trp

To 0.5 mg of Asp-Gly-Gly-Cys-Gly-Cys-His-Leu-Asp-Ile-Ile-Trp in 300 µl phosphate buffer (Na$_2$HPO$_4$, 0.5 mol/l, pH 8.5), 50 µl of a 0.15 molar trisodium citrate dihydrate solution and 2.5 l of a 0.2 molar tin (II) chloride dihydrate solution are added. A pertechnetate solution (0.4 bis 0.9 mCi) out of a Mo-99/Tc-99m generator is added to the reaction mixture, which is then incubated for 10 min by room temperature. The analysis of labelling is achieved through HPLC.

c) In vivo and In vitro Enrichment of the $^{99m}$Tc-Complex of Asp-Gly-Gly-Cys-Gly-Cys-His-Leu-Asp-Ile-Ile-Trp in WHHL-Rabbits 2 mCi (1 ml) of the analog to b) labelled Asp-Gly-Gly-Cys-Gly-Cys-His-Leu-Asp-Ile-Ile-Trp was applied to a narcotized WHHL-rabbit (Rompun/Ketavet 1:2) via an ear vein. WHHL-rabbits reveal due a missing or defect LDL receptor high LDL levels in blood and therefore show spontaneous arteriosclerotic vascular changes. During the experimental time span of 5 h after application, static photographs with various exposure times and positions were taken with a gamma camera (Elcint SP4 HR). 5 h after application the rabbit was killed and both an autoradiography and a Sudan III dyeing of the aorta were performed. The arteriosclerotic plaques in the region of the aortic arch of the WHHL-rabbits could be depicted with 10 min p.i. in vivo. The subsquent autoradiography performed yielded a labelling of the entire aorta wall as well as the arteriosclerotic plaque. The enrichment factor between the normal and arteriosclerotic wall regions was between 6 and 9, depending on the plaque formation (Sudan III dyeing). The results are summarized in Table 1.

EXAMPLE 2 a) Synthesis of Asp-Gly-Gly-Cys-Gly-Cys-D-Trp-Leu-Asp-Ile-Ile-Trp

Asp-Gly-Gly-Cys-Gly-Cys-D-Trp-Leu-Asp-Ile-Ile-Trp is prepared according to Barany and Marrifield, The Peptides: Analysis, Biology, Academic Press, New York, 1980; Stewart and Young, Solid-Phase Peptide Synthesis, 2nd ed., Pierce Chemical Co., Rockford, Ill., 1984.

| Molecular weight: | calc. | 1337.5 |
| --- | --- | --- |
| | obs. | 1337 (FAB-MS) | b) $^{99m}$Tc-Complex of Asp-Gly-Gly-Cys-Gly-Cys-D-Trp-Leu-Asp-Ile-Ile-Trp

To 0.5 mg of Asp-Gly-Gly-Cys-Gly-Cys-D-Trp-Leu-Asp-Ile-Ile-Trp in 300 μl phosphate buffer ($Na_2HPO_4$, 0.5 mol/l, pH 8.5) 50 μl of 0.15 molar trisodium citrate dihydrate solution and 2.5 μl of 0.2 molar tin (II) chloride dihydrate solution are added. A pertechnetate solution (0.4 bis 0.9 mCi) out of a Mo-99/Tc-99m generator is added to the reaction mixture, which is then incubated 10 min at room temperature. The analysis of labelling is achieved via HPLC.

c) In vivo and In vitro Enrichment of the $^{99m}$Tc-Complex of Asp-Gly-Gly-Cys-Gly-Cys-D-Trp-Leu-Asp-Ile-Ile-Trp in WHHL-Rabbits The in vivo and in vitro enrichment of the $^{99m}$Tc complex of Asp-Gly-Gly-Cys-Gly-Cys-D-Trp-Leu-Asp-Ile-Ile-Trp in WHHL-rabbits was performed as described in Example 1 c). The results are summarized in Table 1.

EXAMPLE 3 a) Synthesis of Asp-Gly-Gly-Cys-Gly-Cys-Phe-(D-Trp)-Leu-Asp-Ile-Ile-Trp

Asp-Gly-Gly-Cys-Gly-Cys-Phe-(D-Trp)-Leu-Asp-Ile-Ile-Trp is prepared according to Barany and Marrifield, The Peptides: Analysis, Biology, Academic Press, New York, 1980; Stewart and Young, Solid-Phase Peptide Synthesis, 2nd ed., Pierce Chemical Co., Rockford, Ill., 1984.

| Molecular weight: | calc. | 1484.68 |
| --- | --- | --- |
| | obs. | 1484 (FAB-MS) | b) $^{99m}$Tc-Complex of Asp-Gly-Gly-Cys-Gly-Cys-Phe-(D-Trp)-Leu-Asp-Ile-Ile-Trp To 0.5 mg of Asp-Gly-Gly-Cys-Gly-Cys-Phe-(D-Trp)-Leu-Asp-Ile-Ile-Trp in 300 μl phosphate buffer ($Na_2HPO_4$, 0.5 mol/l, pH 8.5) 50 μl of a 0.15 molar trisodium citrate dihydrate solution and 2.5 μl of 0.2 molar tin (II) chloride dihydrate solution are added. A pertechnetate solution (0.4 bis 0.9 mCi) out of a Mo-99/Tc-99m generator is added to the reaction mixture, which is then incubated 10 min at room temperature. The analysis of the labelling is achieved through HPLC.

c) In vivo and In vitro Enrichment of Tc-99m-Complex of Asp-Gly-Gly-Cys-Gly-Cys-Phe-(D-Trp)-Leu-Asp-Ile-Ile-Trp in WHHL-Rabbits The in vivo and in vitro enrichment of the Tc-99m-complex of Asp-Gly-Gly-Cys-Gly-Cys-Phe-(D-Trp)-Leu-Asp-Ile-Ile-Trp in WHHL-rabbits was performed as described in Example 1 c). The results are summarized in Table 1.

EXAMPLE 4 a) Synthesis of N-(4-hydroxycarboxy-1-oxo-3-thia-but-1-yl)-Cys-Phe-(D-Trp)-Leu-Asp-Ile-Ile-Trp 109.5 mg (0.1 mmol) $NH_2$-Cys-Phe-(D-Trp)-Leu-Asp-Ile-Ile-Trp (prepared according to: E. Atherton, R. C. Sheppard, Solid phase peptide synthesis, Oxford university press, Oxford, New York, Tokyo) are dissolved, under an argon atmosphere, in 3 ml water-free dimethylformamide under the addition of 30.36 mg (0.3 mmol) triethylamine. At 0° C. 13.21 mg (0.1 mmol) thiodiglycolic acid anhydride are added. Subsequently the solution is stirred 2 h at 0° C. and thereafter overnight at room temperature. The raw peptide is precipitated via the addition of 10 ml water-free diethylether and purified through chromatography on silica gel RP-18 (elute: water/0.1% trifluoroacetic acid, acetonitrile/0.1% trifluoroacetic acid, linear gradient). After lyophilisation a white powder is obtained.

Yield: 48.5 mg (39.5% Th.), white powder

| Molecular weight: | calc. | 1227.4438 |
| --- | --- | --- |
| | obs. | 1227 (FAB-MS) | b) Tc-99m-Complex of N-(4-hydroxycarboxy-1-oxo-3-thia-but-1-yl)-Cys-Phe-(D-Trp)-Leu-Asp-Ile-Ile-Trp 1 mg of the peptide conjugates HOOC—$CH_2$—S—$CH_2$—CONH-Cys-Phe-(D-Trp)-Leu-Asp-Ile-Ile-Trp described in Example 4 a) are dissolved in 500 μl disodium hydrogen phosphate buffer (0.01 mol/l, pH 8.5) and 50 μl of a 0.15 molar trisodium citrate dihydrate solution are added. After the addition of pertechnetate solution (0.4–0.9 mCi) out of a Mo-99/Tc-99m generator, 5 μl of a 0.2 molar tin(II) chloride dihydrate solution are added and the reaction mixture is incubated 10 min at room temperature. The labelling yield is determined through analytical HPLC and is greater 95%.

c) In vivo and In vitro Enrichment of the Tc-99m-Complex of N-(4-hydroxycarboxy-1-oxo-3-thia-but-1-yl)-Cys-Phe-(D-Trp)-Leu-Asp-Ile-Ile-Trp in WHHL-Rabbits The in vivo and in vitro enrichment of the Tc-99m-complex of N-(4-hydroxycarboxy-1-oxo-3-thia-but-1-yl)-Cys-Phe-(D-Trp)-Leu-Asp-Ile-Ile-Trp in WHHL-rabbits was performed as described in Example 1 c). The results are summarized in Table 1.

EXAMPLE 5 a) Synthesis of N-(4-hydroxycarboxy-1-oxo-3-thia-but-1-yl)-Cys-(D-Trp)-Leu-Asp-Ile-Ile-Trp 94.8 mg (0.1 mmol) $NH_2$-Cys-(D-Trp)-Leu-Asp-Ile-Ile-Trp (prepared according to: E. Atherton, R. C. Sheppard, Solid phase peptide synthesis, Oxford university press, Oxford, New York, Tokyo) are dissolved, under argon atmosphere, in 3 ml water-free dimethylformamide under the addition of 30.36 mg (0.3 mmol) triethylamine. At 0° C. 13.21 mg (0.1 mmol) thiodiglycolic acid anhydride are added. Subsequently the solution was stirred 2 h at 0° C. and thereafter overnight at room temperature. The raw peptide is precipitated through the addition of 10 ml water-free diethylether and purified through chromatography on silica gel RP-18 (elute: water/0.1% trifluoroacetic acid, aceto-nitrile/0.1% trifluoroacetic acid, linear gradient). After lyophilisation a white powder is obtained.

Yield: 39.3 mg (36.4% Th.), white powder

| Molecular weight: | calc. | 1080.2738 |
|---|---|---|
| | obs. | 1080 (FAB-MS) | b) Tc-99m-Complex of N-(4-hydroxycarboxy-1-oxo-3-thia-but-1-yl)-Cys-(D-Trp)-Leu-Asp-Ile-Ile-Trp 1 mg of the peptide conjugate HOOC—CH$_2$—S—CH$_2$—CONH-Cys-(D-Trp)-Leu-Asp-Ile-Ile-Trp described in Example 5 a) is dissolved in 500 μl disodium hydrogen phosphate buffer (0.01 mol/l, pH 8.5) and 50 μl of a 0.15 molar trisodium citrate dihydrate solution are added. After addition of pertechnetate solution (0.4–0.9 mCi) out of a Mo-99/Tc-99m generator, 5 μl of a 0.2 molar tin(II) chloride dihydrate solution are added and the reaction mixture is incubated 10 min at room temperature. The labelling yield was determined through analytical HPLC and is greater than 95%.

c) In vivo and In vitro Enrichment of the Tc-99m-Complex of N-(4-hydroxycarboxy-1-oxo-3-thia-but-1-yl)-Cys-(D-Trp)-Leu-Asp-Ile-Ile-Trp in WHHL-Rabbits The in vivo and in vitro enrichment of the Tc-99m-complex of N-(4-hydroxycarboxy-1-oxo-3-thia-but-1-yl)-Cys-(D-Trp)-Leu-Asp-Ile-Ile-Trp in WHHL-rabbits was performed as described in Example 1 c). The results are summarized in Table 1.

EXAMPLE 6 a) Synthesis of N-(4-hydroxycarboxy-1-oxo-3-thia-but-1-yl)-Cys-His-Leu-Asp-Ile-Ile-Trp 89.9 mg (0.1 mmol) NH$_2$-Cys-His-Leu-Asp-Ile-Ile-Trp (prepared according to: E. Atherton, R. C. Sheppard, Solid phase peptide synthesis, Oxford university press, Oxford, New York, Tokyo) are dissolved, under argon atmosphere, in 3 ml water-free dimethylformamide under the addition of 30.36 mg (0.3 mmol) triethylamine. At 0° C. 13.21 mg (0.1 mmol) thiodiglycolic acid anhydride are added. Subsequently stirred 2 h at 0° C. and thereafter overnight at room temperature. The raw peptide is precipitated through the addition of 10 ml water-free diethylether and purified through chromatography on silica gel RP-18 (elute: water/0.1% trifluoroacetic acid, acetonitrile/0.1% trifluoroacetic acid, linear gradient). After lyophilisation a white powder is obtained.

Yield: 26.9 mg (26.1% Th.), white powder

| Molecular weight: | calc. | 1031.2038 |
|---|---|---|
| | obs. | 1031 (FAB-MS) | b) Tc-99m-Complex von N-(4-hydroxycarboxy-1-oxo-3-thia-but-1-yl)-Cys-His-Leu-Asp-Ile-Ile-Trp 1 mg of the peptide conjugates described in Example 6 a) HOOC—CH$_2$—S—CH$_2$—CONH-Cys-His-Leu-Asp-Ile-Ile-Trp is dissolved in 500 μl disodium hydrogen phosphate buffer (0.01 mol/l, pH 8.5) and 50 μl of a 0.15 molar trisodium citrate dihydrate solution are added. After the addition of pertechnetate solution (0.4–0.9 mCi) out of a Mo-99/Tc-99m generator, 5 μl of a 0.2 molar tin(II) chloride dihydrate solution are added and the reaction mixture is incubated 10 min at room temperature. The labelling yield is determined via analytical HPLC and is greater than 95%.

c) In vivo and In vitro Enrichment of the Tc-99m-Complex of N-(4-hydroxycarboxy-1-oxo-3-thia-but-1-yl)-Cys-His-Leu-Asp-Ile-Ile-Trp in WHHL-Rabbits The in vivo and in vitro enrichment of the Tc-99m-complex of N-(4-hydroxycarboxy-1-oxo-3-thia-but-1-yl)-Cys-His-Leu-Asp-Ile-Ile-Trp in WHHL-rabbits was performed as described in Example 1 c). The results are summarized in Table 1.

EXAMPLE 7 a) Synthesis of N-(mercaptoacetyl)-Gly-Gly-Asp-Phe-(D-Trp)-Leu-Asp-Ile-Ile-Trp 122.1 mg (0.1 mmol) NH$_2$-Gly-Gly-Asp-Phe-(D-Trp)-Leu-Asp-Ile-Ile-Trp (prepared according to: E. Atherton, R. C. Sheppard, Solid phase peptide synthesis, Oxford university press, Oxford, New York, Tokyo) are dissolved, under argon atmosphere, in 3 ml water-free dimethylformamide under the addition of 40.48 mg (0.4 mmol) triethylamine. At 0° C. a solution of S-tritylmercaptoacetic acid-N-hydroxysuccinimidester in 3 ml water-free dimethylformamide [Preparation: 36.79 mg (0.11 mmol) S-tritylmercaptoacetic acid are dissolved under the addition of 12.66 mg (0.11 mmol) N-hydroxysuccinimide in 2 ml water-free dimethylformamide. A solution of 22.70 mg (0.11 mmol) dicyclohexylcarbodiimide in 1 ml water-free dimethylformamide is added and incubated 30 min. After filtering, the in situ prepared S-tritylmercaptoacetic acid-N-hydroxysuccinimide ester solution can be used in the coupling.] Subsequently stirred 2 h at 0° C. and thereafter overnight at room temperature. The raw peptide is precipitated via the addition of 20 ml water-free diethylether and stirred for 10 min in 5 ml trifluoroacetic acid/5% water/22 mg tributylsilane under argon atmosphere. The raw peptide without protective group is isolated through precipitation with 25 ml water-free diethylether and purified through chromatography on silica gel RP-18 (elute: water/0.1% trifluoroacetic acid, acetonitrile/0.1% trifluoroacetic acid, linear gradient). After lyophilisation a white powder is obtained.

Yield: 56.3 mg (43.4% Th.), white powder

| Molecular weight: | calc. | 1296.4551 |
|---|---|---|
| | obs. | 1296 (FAB-MS) | b) Tc-99m-Complex of N-(mercaptoacetyl)-Gly-Gly-Asp-Phe-(D-Trp)-Leu-Asp-Ile-Ile-Trp 1 mg of the peptide conjugate described in Example 7 a) HS—CH$_2$—CONH-Gly-Gly-Asp-Phe-(D-Trp)-Leu-Asp-Ile-Ile-Trp is dissolved in 500 μl disodium hydrogen phosphate buffer (0.01 mol/l, pH 8.5) and 50 μl of 0.15 molar trisodium citrate dihydrate solution are added. After addition of pertechnetate solution (0.4–0.9 mCi) out of Mo-99/Tc-99m generator, 5 μl of 0.2 molar tin(II) chloride dihydrate solution are added and the reaction mixture is incubated 10 min at room temperature. The labelling yield was determined through analytical HPLC and is greater than 98%.

c) In vivo and In vitro Enrichment of Tc-99m-Complex of N-(mercaptoacetyl)-Gly-Gly-Asp-Phe-(D-Trp)-Leu-Asp-Ile-Ile-Trp in WHHL-Rabbits The in vivo and in vitro enrichment of the Tc-99m-complex of N-(mercaptoacetyl)-Gly-Gly-Asp-Phe-(D-Trp)-Leu-Asp-Ile-Ile-Trp in WHHL-rabbits was performed as described in Example 1 c). The results are summarized in Table 1.

EXAMPLE 8 a) Synthesis of N-(mercaptoacetyl)-Gly-Gly-Asp-(D-Trp)-Leu-Asp-Ile-Ile-Trp 107.4 mg (0.1 mmol) NH$_2$-Gly-Gly-Asp-(D-Trp)-Leu-Asp-Ile-Ile-Trp (prepared in according to: E. Atherton, R. C. Sheppard, Solid phase peptide synthesis, Oxford university press, Oxford, New York, Tokyo) are dissolved, under argon atmosphere, in 3 ml water-free dimethylformamide under the addition of 40.48 mg (0.4 mmol) triethylamine. At 0° C. a solution of S-trityl-mercaptoacetic acid-N-hydroxysuccinimidester in 3 ml water-free dimethylformamide [preparation: 36.79 mg (0.11 mmol) S-trityl-mercaptoacetic acid dissolved under the addition of 12.66 mg (0.11 mmol) N-hydroxysuccinimide in 2 ml water-free dimethylformamide. A solution of 22.70 mg (0.11 mmol) dicyclohexylcarbodiimide in 1 ml water-free dimethylformamide is added and incubated 30 min. After filtering, the in situ so-prepared S-trityl-mercaptoacetic acidic N-hydroxysuccinimidester solution can be used for coupling.] Subsequently stirred 2 h at 0° C. and thereafter overnight at room temperature. The raw peptide is precipitated through the addition of 20 ml water-free diethylether and stirred for 10 min in 5 ml trifluoroacetic acid/5% water/22 mg tributylsilane under argon atmosphere. The raw peptide free of the protective group is obtained through the precipitation with 25 ml water-free diethylether and purified through chromatography on silica gel RP-18 (elute: water/ 0.1% trifluoroacetic acid, acetonitrile/0.1% trifluoroacetic acid, linear gradient). After lyophilisation a white powder is obtained.

Yield: 46.3 mg (40.3% Th.), white powder

| Molecular weight: | calc. | 1049.2851 |
| --- | --- | --- |
| | obs. | 1049 (FAB-MS) | b) Tc-99m-Complex of N-(mercaptoacetyl)-Gly-Gly-Asp-(D-Trp)-Leu-Asp-Ile-Ile-Trp 1 mg of the peptide conjugate described in Example 8 a) HS—CH$_2$—CONH-Gly-Gly-Asp-(D-Trp)-Leu-Asp-Ile-Ile-Trp is dissolved in 500 µl disodium hydrogen phosphate buffer (0.01 mol/l, pH 8.5) and 50 µl of a 0.15 molar trisodium citrate dihydrate solution are added. After the addition of pertechnenate solution (0.4–0.9 mCi) out of a Mo-99/Tc-99m generator, 5 µl of a 0.2 molar tin(II) chloride dihydrate solution are added and incubated 10 min at room temperature. The labelling yield is determined through analytical HPLC and is greater then 97%.

c) In vivo and In vitro Enrichment of the Tc-99m-Complex of N-(mercaptoacetyl)-Gly-Gly-Asp-(D-Trp)-Leu-Asp-Ile-Ile-Trp in WHHL-Rabbits The in vivo and in vitro enrichment of the Tc-99m-complex of N-(mercaptoacetyl)-Gly-Gly-Asp-(D-Trp)-Leu-Asp-Ile-Ile-Trp in WHHL-rabbits was performed as described in Example 1 c). The results are summarized in Table 1.

Figure 1:
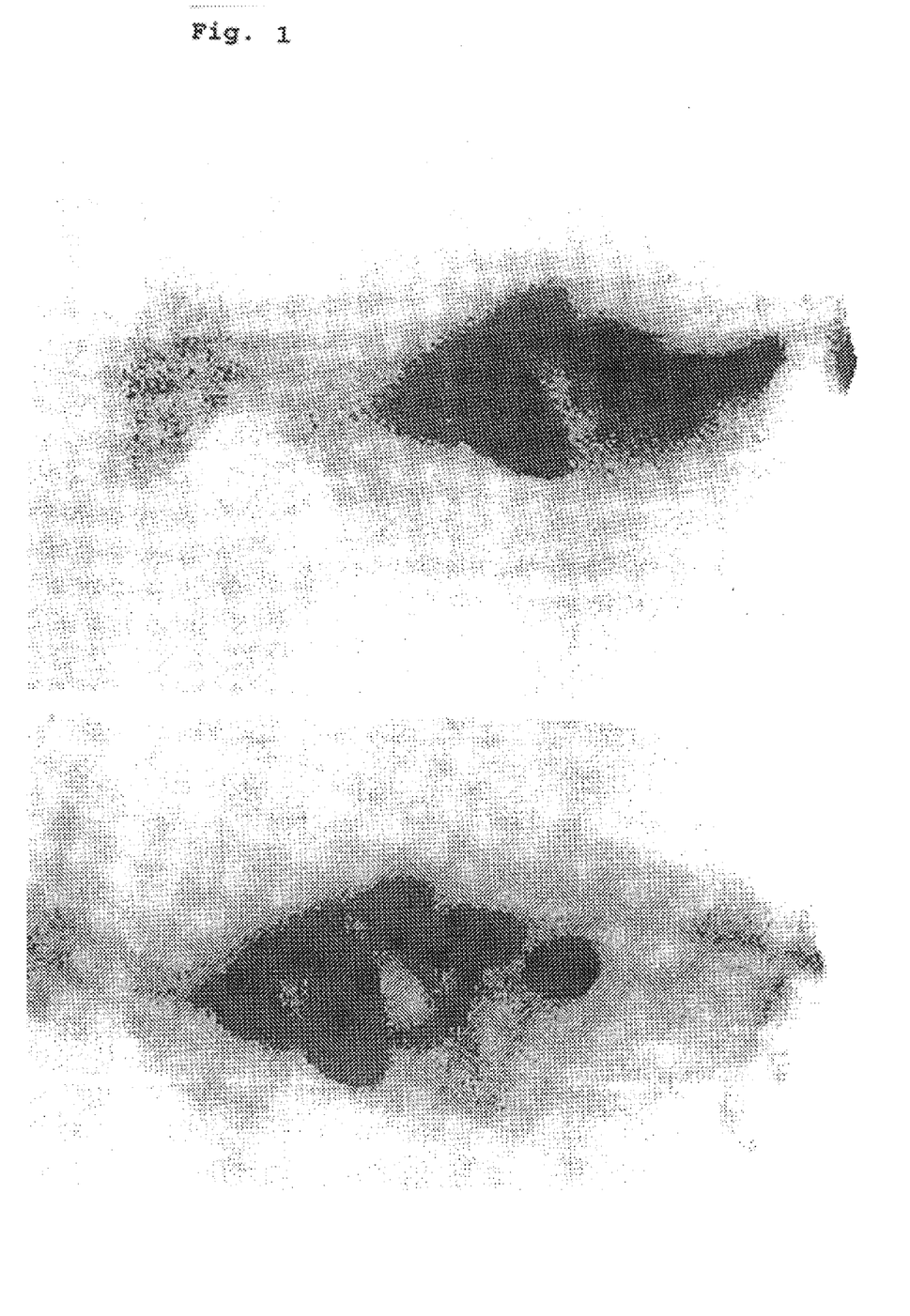

A left lateral scintigram of a WHHL-rabbit (A) and a New Zealand control rabbit (B) 0.5 h after i. v. application of 74 MBq Tc-99m-Asp-Gly-Gly-Cys-Gly-Cys-Phe-(D-Trp)-Leu-Asp-Ile-Ile-Trp (cf. Example 3 c) show observable enrichment activity in vivo in the region of the aortic arch, the left a. carotis as well as in region of the abdominal aorta of the WHHL-rabbit (A) in contrast to control rabbit (B).

Figure 2:
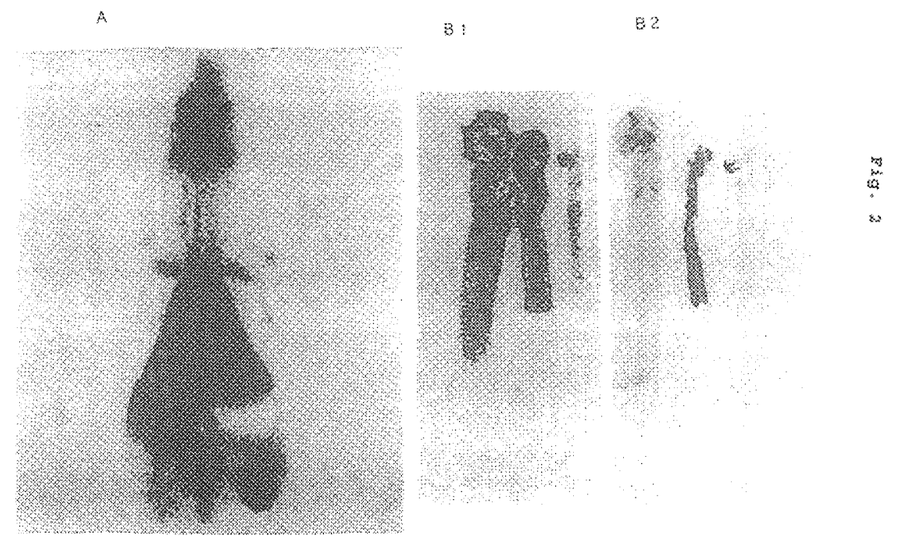

An anterior scintigram of a New Zealand rabbit whose right a. carotis was denuded four weeks earlier with the help of a Fogarty-catheter (A) 0.5 h after i.v. application of 74 MBq Tc-99m-Asp-Gly-Gly-Cys-Gly-Cys-(D-Trp)-Leu-Asp-Ile-Ile-Trp, as well as an autoradiogram (B1) and Sudan-III-dyeing (B2) of the thoracic aorta removed 5 h after i.v. application, of the denuded and untreated a. carotis (cf. Example 3 c) show the order of the dissected tissue for each B1 and B2 from left to right: thoracic aorta, right denuded a. carotis and left untreated a. carotis.

The strongly arteriosclerotic right a. carotis could be detected in vivo (A). The in vitro investigation (B) confirms the good correlation between the high and selective accumulation of radiopharmaceutical in the denuded right a. carotis in comparison to the untreated left a. carotis.

What is claimed is:

1. A compound of formula I

$$(K)_z\text{-}(L)_y\text{-}(A^1)_{aa}\text{-}(A^2)_{bb}\text{-}(A^3)_{cc}\text{-}(A^4)_{dd}\text{-}(A^5)_{ee}\text{-}(A^6)_{ff}\text{-}(A^7)_{gg}\text{-}(A^8)_{hh}\text{-}$$
$$(A^9)_{jj}\text{-}(A^{10})_{kk}\text{-}(A^{11})_{ll}\text{-}\text{Ile-Ile-Trp} \quad (I)$$

in which
aa, bb, cc, dd, ee, ff, gg, hh, jj, kk and ll are each, independent from one another, 0, 1 or 2,
y and z are each, independent from one another, 0 or 1,
K is a chelate-forming residual having the formula IIA or IIB in which
T is a hydrogen atom or a bond at a metal atom or a sulfur protective group or wherein two T residuals form together with the attached S atoms inter- or intramolecular disulfide bridges, wherein $R_4$ is of the formula IIC or IID wherein
the *-marked carbon atoms are bound to the amino groups of the formula IIB,
n' is 1 or 2,
i is from 2 to 6, and
TT is an α-amino acid group bonded by its amino group to form an amide group,
or is:
a chelate-forming residual having the formula IIE in which
$R_6$ represents a hydrogen or a $C_{1-6}$-alkyl group, or K is chelate-forming residual having the formula IIF (IIF)

in which
R$_7$ to R$_{18}$ each are independent from one another a hydrogen atom, a C$_{1-10}$-alkyl chain or a bond on L; o; p and r each are 1 or 2; and T has the above meaning,
or K is a chelate-forming residual having the formula IIG (IIG)

in which
R$_{19}$ to R$_{24}$ are the same or different and are each, independent from one another, a hydrogen atom or a C$_{1-4}$-alkyl group, and m' is 2 or 3,
or K is a chelate-forming residual having the formula IIH (IIH)

in which
X$_1$ is a bond, a methylene group or a CHY$_4$-group, and one of the groups Y$_1$, Y$_2$, Y$_3$ or Y$_4$ is a bond to L and the remaining groups are independently a hydrogen or oxygen atom,
T has the above given meaning, and
A$_1$, A$_2$, A$_3$ and A$_4$ are equal or different and are each, independent from one another, hydrogen or a C$_{1-6}$-alkyl group,
or K is a chelate-forming residual having the formula IIJ (IIJ)

in which
R$_{27}$ is a hydrogen atom or a C$_{1-6}$-alkyl group substituted with one or two hydroxyl groups,

R$_{25}$ and R$_{26}$ are each a hydrogen atom or together a carbonyl oxygen atom,
A is a hydroxyl- or mercapto group,
Y is a hydrogen atom, or a carboxy- or sulfonyl group and
Z is a carbon atom or a nitrogen atom,
or K is a chelate-forming residual having the formula IIK, $(AA^1)_{mm}$-$(AA^2)_{nn}$-$(AA^3)_{oo}$-$(AA^4)_{pp}$-$(AA^5)_{qq}$-$(AA^6)_{rr}$    (IIK)

in which
mm, nn, oo, pp, qq and rr are each, independent from one another, 0, 1 or 2,
AA$^1$ to AA$^6$ are each, independent from one another, an α-amino acid group bonded by its amino group to form an amide with the adjoining α-amino acid, wherein optionally two available cysteine α-amino acid groups are linked to one another to form one cysteine α-amino acid group,
or K is a chelating group having the formula IIL, in which
R$^a$, R$^b$, R$^c$, R$^d$, R$^f$, R$^g$ and R$^h$ are the same or different and each is a hydrogen atom or a branched or non-branched C$_{1-6}$-alkyl group,
R$^e$ is a carboxy group or a non-branched, branched, cyclic or polycyclic C$_1$–C$_{60}$-alkyl-, alkenyl-, polyalkenyl-, alkinyl-, polyalkinyl-, aryl-, alkylaryl- or arylalkyl group, which is optionally substituted with hydroxy-, oxy-, oxo-, carboxy-, amninocarbonyl-, alkoxycarbonyl-, amino-, aldehyde- or alkoxy groups having up to 20 carbon atoms and/or optionally interrupted by one or more optionally substituted heteroatoms from O, N, S, P, As, and Se,
T has the above meaning,
L is a bond or a hydrogen atom or a non-branched, branched, cyclic or polycyclic C$_1$–C$_{60}$-alkyl, alkenyl-, polyalkenyl-, alkinyl-, polyalkenyl, aryl-, alkylaryl- or arylalkyl group, which is optionally substituted with one or more hydroxy-, mercapto-, alkylmercapto-, oxo-, oxy-, carboxy-, aminocarbonyl-, alkoxycarbonyl-, amino-, aldehyde- or alkoxy groups having up to 20 carbon atoms and/or optionally interrupted by one or more optionally substituted heteroatoms from O, N, S, P, As, Se,
or L is a Z$_1$—R—Z$_2$ group,
in which
R is a straight chain, branched, saturated or unsaturated C$_{1-20}$ alkyl group which is optionally interrupted by one or more oxygen and/or sulfur atoms and/or carbonyl-, —NHCO—, —N(C$_{1-6}$-alkyl)CO—, —NH— and —N(C$_{1-6}$-alkyl)-groups and optionally substituted with hydroxy and/or epoxy groups,
Z$_1$ and Z$_2$, independent from one another, each are an —O—, —S—, —(C=O)O—, —NH(C=S)NH—, —(C=O)— or —NH(C=S)— group or a group having the formula α in which
s and t are each, independent from one another, 0, 1, 2 or 3, the ring B is a phenyl- or cyclohexyl residual and $Z_1$ and $Z_2$ have the above given meaning, $A^1$ to $A^{11}$ are each, independent from one another, a L-α- or D-α-amino acid group, —NH—CH(Z)—CO— group, in which
Z is
H—, $CH_3$—, $(CH_3)_2CH$—, $(CH_3)_2CH$—$CH_2$—, $CH_3$—$CH_2$—$CH(CH_3)$—, $CH_3$—S—$(CH_2)_2$—, HOOC—$CH_2$—,
HOOC—$(CH_2)_2$—, $H_2N$—$(CH_2)_3$—, $H_2N$—C(=NH)—$(CH_2)_3$—,
HO—$CH_2$—, $CH_3$—CH(OH)—, HS—$CH_2$—, HS—$CH_2$—, HS—$(CH_2)_2$—,
$H_2N$—CO—$CH_2$—, $H_2N$—CO—$(CH_2)_2$—, $(HOOC)_2$CH—$CH_2$—, in which n is 0, 1 or 2,
or Z is group or a taurine group,
as well as complexes of these compounds with metal ions having atomic numbers 21–32, 37–39, 49–51 or 57–83 and their water-soluble salts.

2. A compound of claim 1, wherein the sulfur protective groups for T are selected from the group consisting of an alkali metal ion, a $C_{1-6}$-acyl group, a benzoyl group, a hydroxyacetyl group, an acetamido-methyl group, a p-methoxybenzyl group, an ethoxyethyl group, a benzyl group, an ortho- or para-hydroxybenzyl group, an ortho- or para-acetoxybenzyl groupo, a p-nitrobenzyl group, a 4-picolyl group, a 2-picolyl-N-oxide group, a 9-anthrylmethyl group, a 9-fluoroenyl group, a ferrocenylmethyl group, a diphenylmethyl group, a bis(4-methoxyphenyl)methyl group, a dibenzosuberyl group, a triphenylmethyl group, a diphenyl-4-pyridylmethyl group, a phenyl group, a 2,4-dinitrophenyl group, a-tert.-butyl group, a 1-adamantyl group, a methoxymethyl group, a isobutoxymethyl group, a 2-tetrahydropyranyl group, a benzylthiomethyl group, a phenylthiomethyl group, a trimethylacetamidomethyl group, a benzamidomethyl group, an acetylmethyl group, a carboxymethyl group, a cyanomethyl group, a 2-nitro-1-phenylethyl group, a 2-(4'-pyridyl)ethyl group, a 2-cyanoethyl group, a 2,2-bis(carboethoxy)ethyl group, a 1-m-nitrophenyl-2-benzoylethyl group, a 2-phenylsulfonylethyl group, a 1-(4-methylphenylsulfonyl)-2-methylprop-2-yl group, a silyl group, a N-{[(p-biphenyl)isopropoxy]carbonyl}-N-methyl-γ-aminoburyrate group, a N-(tert-butoxycarbonyl)-N-methyl-γ-aminobutyrate group, a 2,2,2-trichloroethoxycarbonyl group, a tert.-butoxycarbonyl group, a benxyloxycarbonyl group, a p-methoxybenzyloxycarbonyl group, a N-ethyl group, a N-methoxymethyl group, a S-ethyl group, a tert-S-butyl group, a substituted S-phenyl group, a sulfonate group, a sulfenylthiocarbonate group or a 3-nitro-2-pyridinsulfenyl group.

3. A compound of claim 1, wherein the α-amino acid group for TT is selected from the group consisting of alanine, valine, leucine, isoleucine, proline, tryptophane, phenylalanine, methionine, glycine, serine, tyrosine, threonine, cysteine, asparagine, glutamine, aspartic acid, glutamic acid, lysine, arginine, histidine, citrulline, homocysteine, homoserine, 4-hydroxyproline, 5-hydroxylysine, ornithine, sarcosine or taurine and their homologous β-amino acids.

4. A compound of claim 1, wherein the α-amino acid groups for to $AA^1$ are $AA^6$ are selected from the group consisting of alanine, valine, leucine, isoleucine, proline, tryptophane, phenylalanine, methionine, glycine, serine, tyrosmne, threonine, cysteine, which optionally bears a T group with the above given meaning instead of the hydrogen atom on the sulfur, asparagine, glutamine, asparagine acid, glutamine acid, lysine, arginine, histidine, citrulline, homocysteine, homoserine, 4-hydroxyproline, 5-hydroxylysine, ornithine, sarcosine or taurine and/or their homologous β-amino acids.

5. A compound according to claim 1, namely
Tc-99m-complex of Asp-Gly-Gly-Cys-Gly-Cys-His-Leu-Asp-Ile-Ile-Trp,
Tc-99m-complex of Asp-Gly-Gly-Cys-Gly-Cys-(D-Trp)-Leu-Asp-Ile-Ile-Trp,
Tc-99m-complex of Asp-Gly-Gly-Cys-Gly-Cys-Phe-(D-Trp)-Leu-Asp-Ile-Ile-Trp,
Tc-99m-complex of N-(4-hydroxycarboxy-1-oxo-3-thia-but-1-yl)-Cys-Phe-(D-Trp)-Leu-Asp-Ile-Ile-Trp,
Tc-99m-complex of N-(4-hydroxycarboxy-1-oxo-3-thia-but-1-yl)-Cys-(D-Trp)-Leu-Asp-Ile-Ile-Trp,
Tc-99m-complex of N-(4-hydroxycarboxy-1-oxo-3-thia-but-1-yl)-Cys-His-Leu-Asp-Ile-Ile-Trp,
Tc-99m-complex of N-(mercaptoacetyl)-Gly-Gly-Asp-Phe-(D-Trp)-Leu-Asp-Ile-Ile-Trp and
Tc-99m-complex of N-(mercaptoacetyl)-Gly-Gly-Asp-(D-Trp)-Leu-Asp-Ile-Ile-Trp.

6. A compound according to claim 1, namely
Asp-Gly-Gly-Cys-Gly-Cys-His-Leu-Asp-Ile-Ile-Trp,
Asp-Gly-Gly-Cys-Gly-Cys-(D-Trp)-Leu-Asp-Ile-Ile-Trp,
Asp-Gly-Gly-Cys-Gly-Cys-Phe-(D-Trp)-Leu-Asp-Ile-Ile-Trp, N-(4-hydroxycarboxy-1-oxo-3-thia-but-1-yl)-Cys-Phe-(D-Trp)-Leu-Asp-Ile-Ile-Trp,

N-(4-hydroxycarboxy-1-oxo-3-thia-but-1-yl)-Cys-(D-Trp)-Leu-Asp-Ile-Ile-Trp, N-(4-hydroxycarboxy-1-oxo-3-thia-but-1-yl)-Cys-His-Leu-Asp-Ile-Ile-Trp, N-(mercaptoacetyl)Gly-Gly-Asp-Phe-(D-Trp)-Leu-Asp-Ile-Ile-Trp and N-(mercaptoacetyl)-Gly-Gly-Asp-(D-Trp)-Leu-Asp-Ile-Ile-Trp.

7. A process for the production of a compound according to claim 1, comprising reacting a compound of the formula II (II)

in which

A$^1$ to A$^{11}$, aa, bb, cc, dd, ee, ff, gg, hh, jj, kk and ll have the meaning defined in claim 1, with a compound having the formula III (III)

wherein

K, L, z and y have the meaning as defined in claim 1, and optionally further reacting with a radioactive metal ion in its permetallate form in the presence of a reducing agent and optionally auxiliary ligands, or with a salt or oxide of a radioactive cation.

8. A diagnostic agent comprising a compound of claim 1 and, optionally, pharmaceutically acceptable adjuvants and excipients.

9. A diagnostic agent of claim 8, wherein the compound is complexed with at least one metal ion of atomic numbers 21–32, 37–39, 42–51 or 57–83.

10. A method for the diagnosis of arteriosclerosis which comprises administering to a patient a compound of claim 1 which is complexed with at least one metal ion of atomic number 21–32, 37–39, 42–51 or 57–83.

11. The method of claim 10, wherein the at least one metal ion is a radioactive labeled metal ion.

12. The method of claim 10, further comprising displaying concentrations of the complexed compound at arteriosclerotic vascular lesions.

13. The method of claim 12, wherein the display is by scintillation camera.

14. The method of claim 10, wherein the complexed compound is administered in a dose of $1\times10^{-5}$ to $5\times10^4$ nmol/kg body weight of the patient.

15. A compound of claim 1, which is complexed with at least one $^{99m}$Tc or Re metal ion.

* * * * *

UNITED STATES PATENT AND TRADEMARK OFFICE
CERTIFICATE OF CORRECTION

PATENT NO. : 6,342,201 B1
DATED : January 29, 2002
INVENTOR(S) : Ludger Dinkelborg et al.

It is certified that error appears in the above-identified patent and that said Letters Patent is hereby corrected as shown below:

Column 26,
Line 48, reads "bound to the amino" should read -- bound to the imino --
Line 54, reads "or is" should read -- or K is --

Column 30,
Line 39, reads "tyrosmne, threonine" should read -- tyrosine, threonine --

Column 31,
Line 7, reads "(mercaptoacetyl) Gly-" should read -- (mercaptoacetyl)-Gly- --

Signed and Sealed this

First Day of April, 2003

JAMES E. ROGAN
*Director of the United States Patent and Trademark Office*

SEQUENCE LISTING (1) GENERAL INFORMATION:

(iii) NUMBER OF SEQUENCES:  10

(2) INFORMATION FOR SEQ ID NO:1:

(i) SEQUENCE CHARACTERISTICS:
        (A) LENGTH:   21 amino acids
        (B) TYPE:  amino acid
        (C) STRANDEDNESS:  single
        (D) TOPOLOGY:  linear (ii) MOLECULE TYPE:  peptide (iii) HYPOTHETICAL:  NO (iv) ANTI-SENSE:  NO (v) FRAGMENT TYPE:  internal (xi) SEQUENCE DESCRIPTION:   SEQ ID NO:1:

Cys  Ser  Cys  Ser  Ser  Leu  Met  Asp  Lys  Glu  Cys  Val  Tyr  Phe
1                     5                              10

Cys  His  Leu  Asp  Ile  Ile  Trp
15                    20

(2) INFORMATION FOR SEQ ID NO:2:

```
        (i) SEQUENCE CHARACTERISTICS:
             (A) LENGTH:  12 amino acids
             (B) TYPE:  amino acid
             (C) STRANDEDNESS:  single
             (D) TOPOLOGY:  linear (ii) MOLECULE TYPE:  peptide (iii) HYPOTHETICAL:  NO (iv) ANTI-SENSE:  NO (v) FRAGMENT TYPE:  internal (xi) SEQUENCE DESCRIPTION:  SEQ ID NO:2:

Asp Gly Gly Cys Gly Cys His Leu Asp Ile Ile Trp
1               5                   10

(2) INFORMATION FOR SEQ ID NO:3:

(i) SEQUENCE CHARACTERISTICS:
             (A) LENGTH:  12 amino acids
             (B) TYPE:  amino acid
             (C) STRANDEDNESS:  single
             (D) TOPOLOGY:  linear (ii) MOLECULE TYPE:  peptide (iii) HYPOTHETICAL:  NO (iv) ANTI-SENSE:  NO (v) FRAGMENT TYPE:  internal (xi) SEQUENCE DESCRIPTION:  SEQ ID NO:3:

Asp Gly Gly Cys Gly Cys Trp Leu Asp Ile Ile Trp
1               5                   10

(2) INFORMATION FOR SEQ ID NO:4:

(i) SEQUENCE CHARACTERISTICS:
             (A) LENGTH:  13 amino acids
             (B) TYPE:  amino acid
             (C) STRANDEDNESS:  single
             (D) TOPOLOGY:  linear (ii) MOLECULE TYPE:  peptide (iii) HYPOTHETICAL:  NO (iv) ANTI-SENSE:  NO (v) FRAGMENT TYPE:  internal (xi) SEQUENCE DESCRIPTION:  SEQ ID NO:4:

Asp Gly Gly Cys Gly Cys Phe Trp Leu Asp Ile Ile Trp
1               5                   10

(2) INFORMATION FOR SEQ ID NO:5:

(i) SEQUENCE CHARACTERISTICS:
             (A) LENGTH:  8 amino acids
             (B) TYPE:  amino acid
             (C) STRANDEDNESS:  single
             (D) TOPOLOGY:  linear (ii) MOLECULE TYPE:  peptide (iii) HYPOTHETICAL:  NO (iv) ANTI-SENSE:  NO
```

(v) FRAGMENT TYPE:  internal (xi) SEQUENCE DESCRIPTION:  SEQ ID NO:5:

Cys  Phe  Trp  Leu  Asp  Ile  Ile  Trp
1                        5

(2) INFORMATION FOR SEQ ID NO:6:

(i) SEQUENCE CHARACTERISTICS:
        (A) LENGTH:  7 amino acids
        (B) TYPE:  amino acid
        (C) STRANDEDNESS:  single
        (D) TOPOLOGY:  linear (ii) MOLECULE TYPE:  peptide (iii) HYPOTHETICAL:  NO (iv) ANTI-SENSE:  NO (v) FRAGMENT TYPE:  internal (xi) SEQUENCE DESCRIPTION:  SEQ ID NO:6:

Cys  Trp  Leu  Asp  Ile  Ile  Trp
1                   5

(2) INFORMATION FOR SEQ ID NO:7:

(i) SEQUENCE CHARACTERISTICS:
        (A) LENGTH:  7 amino acids
        (B) TYPE:  amino acid
        (C) STRANDEDNESS:  single
        (D) TOPOLOGY:  linear (ii) MOLECULE TYPE:  peptide (iii) HYPOTHETICAL:  NO (iv) ANTI-SENSE:  NO (v) FRAGMENT TYPE:  internal (xi) SEQUENCE DESCRIPTION:  SEQ ID NO:7:

Cys  His  Leu  Asp  Ile  Ile  Trp
1                   5

(2) INFORMATION FOR SEQ ID NO:8:

(i) SEQUENCE CHARACTERISTICS:
        (A) LENGTH:  10 amino acids
        (B) TYPE:  amino acid
        (C) STRANDEDNESS:  single
        (D) TOPOLOGY:  linear (ii) MOLECULE TYPE:  peptide (iii) HYPOTHETICAL:  NO (iv) ANTI-SENSE:  NO (v) FRAGMENT TYPE:  internal (xi) SEQUENCE DESCRIPTION:  SEQ ID NO:8:

Gly  Gly  Asp  Phe  Trp  Leu  Asp  Ile  Ile  Trp
1                   5                         10

(2) INFORMATION FOR SEQ ID NO:9:

(i) SEQUENCE CHARACTERISTICS:
        (A) LENGTH:  9 amino acids
        (B) TYPE:  amino acid

```
            (C) STRANDEDNESS:  single
            (D) TOPOLOGY:  linear (ii) MOLECULE TYPE:  peptide (iii) HYPOTHETICAL:  NO (iv) ANTI-SENSE:  NO (v) FRAGMENT TYPE:  internal (xi) SEQUENCE DESCRIPTION:  SEQ ID NO:9:

Gly  Gly  Asp  Trp  Leu  Asp  Ile  Ile  Trp
1                   5

(2) INFORMATION FOR SEQ ID NO:10:

(i) SEQUENCE CHARACTERISTICS:
            (A) LENGTH:  11 amino acids
            (B) TYPE:  amino acid
            (C) STRANDEDNESS:  single
            (D) TOPOLOGY:  linear (ii) MOLECULE TYPE:  peptide (iii) HYPOTHETICAL:  NO (iv) ANTI-SENSE:  NO (v) FRAGMENT TYPE:  internal (xi) SEQUENCE DESCRIPTION:  SEQ ID NO:10:

Cys  Xaa  Gly  Cys  Xaa  Gly  Gly  Arg  Gly  Asp  Ser
1                   5                        10
```